United States Patent [19]
Schmidt

[11] Patent Number: 5,381,102
[45] Date of Patent: Jan. 10, 1995

[54] DEVICE WITH A CURRENT DIVIDER FOR CONTROLLING ADJUSTMENT OF SIGNALS FROM SENSORS

[75] Inventor: Karl-Heinz Schmidt, Oberwart, Austria

[73] Assignee: Robert Bosch GmbH, Stuttgart, Germany

[21] Appl. No.: 243,423

[22] Filed: May 16, 1994

Related U.S. Application Data

[63] Continuation of Ser. No. 59,712, May 18, 1993, which is a continuation of Ser. No. 874,723, Apr. 27, 1992.

[30] Foreign Application Priority Data

May 10, 1991 [DE] Germany ............... 4115288

[51] Int. Cl.⁶ ............................. G01R 27/26
[52] U.S. Cl. .................... 324/720; 73/23.31; 324/721
[58] Field of Search ............... 324/713, 715, 720, 149, 324/72.5, 601, 721; 73/766, 709, 862.623, 23.21, 23.31; 123/693, 694, 695, 696, 703

[56] References Cited

U.S. PATENT DOCUMENTS

| | | |
|---|---|---|
| 3,412,327 | 11/1968 | Murray ................. 324/149 |
| 4,258,563 | 3/1981 | Yasuda et al. ............ 123/703 X |
| 4,476,096 | 10/1984 | Hoht ..................... 422/96 |
| 4,804,632 | 2/1989 | Schuck et al. ............ 73/23.31 |
| 4,911,016 | 3/1990 | Miyazaki ................. 73/766 |
| 5,037,761 | 8/1991 | Barnett et al. ........... 436/143 |
| 5,042,307 | 8/1991 | Kato ..................... 73/766 |
| 5,055,269 | 10/1991 | Palumbo et al. ........... 73/23.31 |
| 5,066,466 | 11/1991 | Holter et al. ............ 422/98 |
| 5,159,277 | 10/1992 | Mount .................... 324/720 |
| 5,182,519 | 1/1993 | Suzuki ................... 324/720 |
| 5,243,297 | 9/1993 | Perkins et al. ........... 324/721 |

FOREIGN PATENT DOCUMENTS

| | | |
|---|---|---|
| 0114235 | 11/1983 | European Pat. Off. . |
| 3826767 | 8/1988 | Germany . |
| WO8706339 | 10/1987 | WIPO . |
| WO9108441 | 6/1991 | WIPO . |

*Primary Examiner*—Maura K. Regan
*Attorney, Agent, or Firm*—Kenyon & Kenyon

[57] ABSTRACT

A device for adjusting sensor signals, and, in particular, signals supplied to a sensor for detecting an operating parameter of a motor vehicle having an internal combustion engine. The device has adjustment elements and a current divider, which includes at least one adjustable resistor and a second resistor, coupled in series with the sensor.

7 Claims, 1 Drawing Sheet

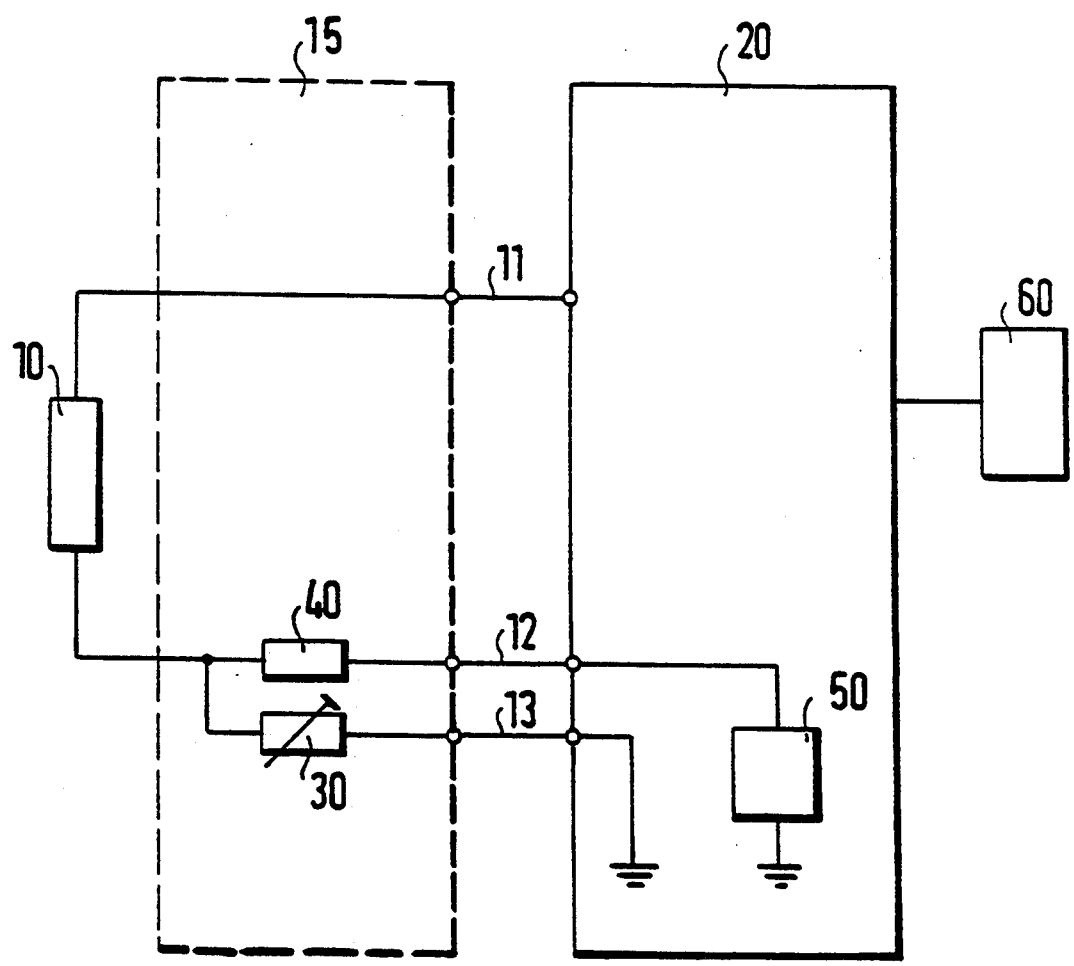

DEVICE WITH A CURRENT DIVIDER FOR CONTROLLING ADJUSTMENT OF SIGNALS FROM SENSORS

CROSS-REFERENCE TO RELATED APPLICATIONS

This application is a continuation of U.S. application Ser. No. 08/059,712 filed on May 18, 1993 which is, in turn, a continuation of U.S. application Ser. No. 07/874,723 filed on Apr. 27, 1992.

FIELD OF THE INVENTION

The present invention relates to a device for adjusting sensor signals, and, in particular, to a device for adjusting an input signal supplied to a sensor which detects an operating parameter of a motor vehicle.

BACKGROUND OF THE INVENTION

A device for adjusting sensor signals is disclosed in European Patent Application No. 0 264 388. This application describes a device for adjusting the output signal of a pressure sensor. To this end, a bridge circuit which comprises two pressure-dependent resistors is connected to an evaluation circuit. The pressure-dependent resistors are used as sensors. Given the same pressure values, resistance values vary from sensor to sensor. To produce a fixed relationship between the quantity to be measured and the output signal from the evaluation circuit, an adjustable resistor is provided. The adjustable resistor is connected in series to the sensor. A compensation circuit, which is quite costly, is required to compensate for the temperature drift of the adjustable resistor. For such devices, the adjustable resistors or the compensation circuit for the temperature drift are usually integrated in the evaluation circuit. As a general rule, if such a sensor is replaced, the evaluation circuit must also be replaced. In addition, the evaluation circuit must be tuned to the specific sensor.

Furthermore, European Patent Application No. 0 114 235 discloses a method for measuring the oxygen content in the exhaust gas of an internal combustion engine. To this end, a defined voltage is applied to a measuring resistor. The current flowing through the resistor is a measure of the oxygen concentration in the exhaust gas. The supply voltage for the measuring resistor is adjusted dependent upon the current measured at the time. It is not foreseen to compensate for variances.

SUMMARY OF THE INVENTION

The present invention provides a device for adjusting an input signal supplied to a sensor which detects an operating parameter of a motor vehicle. The device includes a current divider for measuring an output of the sensor. The current divider is formed by at least two resistors, one of which has a resistance value which is adjustable.

Compared to conventional devices, the device according to the present invention has a very simple construction and enables the sensor to be adjusted simply, with no temperature drift occurring. In addition, if the sensor is replaced, the evaluation circuit does not need to be replaced or readjusted.

The present invention will be explained in detail in the remainder of the specification referring to the drawing.

BRIEF DESCRIPTION OF THE DRAWING

The Figure shows a block diagram of the device according to the present invention.

DETAILED DESCRIPTION OF THE INVENTION

The present invention is a device for adjusting an input signal to a sensor that detects an operating parameter of a motor vehicle.

An oxygen sensor measures the oxygen concentration in the exhaust gas of a diesel gasoline engine. Such an oxygen sensor is disclosed, for example, in European Patent Application No. 0 114 235. Dependent upon the measured oxygen concentration, a controlling device influences a quantity which establishes the power output of the internal combustion engine. Preferably, this quantity is the fuel quantity to be injected. The present invention is able to be applied to this and to other sensors, or to other types of internal combustion engines. Thus, in an advantageous manner, the operation proceeds accordingly for all sensors in which an output quantity of the sensor depends on an operating parameter.

By way of example, in the Figure, a sensor 10 for detecting the oxygen concentration or the oxygen content of the exhaust gas of an internal combustion engine is connected via a probe plug connector 15 and several lines 11, 12 and 13 to a controlling device 20. Starting from the sensor signal, this controlling device calculates a trigger signal for a controlling unit 60. By way of line 11, a terminal of the sensor is loaded with a defined voltage from the controlling device 20. Preferably, the voltage is composed of a dc voltage component of approximately 0.6 V and an ac voltage component. A second terminal of the sensor is connected to the controlling device 20, on the one hand, via a first resistor 30 and line 13 and, on the other hand, via a second resistor 40 and line 12. The first resistor 30, which is also described as an adjustable resistor, is connected directly to ground via line 13. The second resistor 40 is connected to ground via line 12 and a current-measuring device 50. There is a series connection consisting of the sensor 10, the second resistor 40 and the current-measuring device 50. The resistor 30 is connected in parallel to the series connection consisting of the second resistor 40 and the current-measuring device 50. Preferably, the current-measuring device 50 has no internal resistance.

If the defined voltage is applied to the sensor, then the current flowing through the sensor 10 is a measure of the oxygen content in the exhaust gas. The connection between the current and the oxygen content is substantially linear. The relationship between the probe current and the oxygen content, also described as responsivity, is subject to considerable variance, however. The responsivity varies significantly from probe to probe. The variance among the individual probes is far greater than the required measuring accuracy, because not all probes can be manufactured with the same parameters.

To eliminate this variance, conventional devices provide an evaluation circuit which compensates for these variances. However, such devices require that the probe and the evaluation circuit be tuned to one another. This means that each evaluation circuit must be adjusted based on the probe that is utilized. Therefore, when a probe has to be replaced, a new adjustment becomes necessary.

To avoid these disadvantages of conventional devices, the present invention provides adjusting elements arranged directly on the probe or in the probe plug connector. The probe and the adjusting elements constitute a basic unit. Thus, with a given oxygen content for each probe, it is guaranteed that the same output signal is applied to the probe plug connector.

The adjusting resistor has a resistance value that varies depending upon the temperature of the resistor. To permit an exact adjustment, the adjustable resistor must exhibit a nearly constant resistance over a very large temperature range, for instance, a range between $-40°$ and $+130°$. However, such resistors are relatively expensive.

The device according to the present invention provides an alternative. In place of an adjustable resistor, a current divider is utilized. The current divider includes at least two resistors. When the adjustable resistor 30 and the second resistor 40 are appropriately selected, the temperature dependence of the two resistors is the same, provided that the two resistors are properly coupled to one another. Such a proper coupling exists when the two resistors are arranged physically close to one another, and when the resistors have the same temperature for all operating states.

When the probe is adjusted, the adjustable resistance is altered until the current flowing through the second resistor 40 attains a preselected value at a specific oxygen content. The Figure depicts a particularly advantageous embodiment of the present invention, in which the current divider is integrated in the probe plug connector.

It is particularly advantageous when the current divider forms a structural unit with the sensor or with the probe plug connector. When the structural unit including a sensor and current divider, or a probe plug connector and current divider is replaced, no adjustment is necessary. At a particular oxygen content, the same output signal is applied to each probe plug connector.

For the voltage U1 applied to the first resistor, the following relationship exists:

$$U1 = R1*I1$$

where R1 represents the resistance value of the first resistor, and I1 represents the current flowing through the first resistor. For the voltage U2 applied to the second resistor, the following relationship exists:

$$U2 = R2*I2$$

where R2 represents the resistance value of the second resistor, and I2 represents the current flowing through the second resistor.

The probe current IS results from the sum of the two currents I1 and I2. If the internal resistance of the current-measuring device is so small that it can be disregarded, the following relationship exists:

$$I1*R1 = I2*R2$$

The resistance values of the resistors R1 and R2 depend upon the temperature T of the resistors as follows:

$$R1 = RK1*(1 + a*[T-273°])$$

$$R2 = RK2*(1 + a*[T-273°])$$

where RK1 and RK2 represent the temperature-dependent components of the resistors R1 and R2. If the two resistors are thermally coupled in a proper fashion, the following relationship results for the current I2 flowing through the current-measuring device 50:

$$I2 = IS*RK1/(RK1 + RK2)$$

Since RK1 and RK2 represent temperature-independent quantities, the current I2 measured in the current-measuring device is proportional to the probe current, independent of the particular temperature. The variances in the responsivity between the individual sensors can be compensated for by properly selecting the adjustable resistor and/or the second resistor. It is particularly advantageous when the first resistor R1 is altered during the adjustment.

What is claimed is:

1. A device for evaluating a current provided at an output of a sensor, the sensor output current being indicative of a value of a preselected parameter, the device comprising:

a current divider circuit coupled between the output of the sensor and ground, the current divider circuit dividing the sensor output current between first and second current branches of the current divider circuit, the first and second current branches being coupled in parallel;

the first current branch including a first resistor having a resistance value that is adjustable for controlling the division of the sensor output current between the first and second current branches in order to provide a preselected current through the second current branch of the current divider circuit for a preselected value of the preselected parameter, the first resistor having a predetermined temperature dependence;

the second current branch including a second resistor coupled in series with a current measuring device, the second resistor having the predetermined temperature dependence and being arranged physically close to the first resistor such that the division of the sensor output current between the first and second current branches is independent of temperature, the current measuring device measuring a portion of the sensor output current flowing through the second current branch and thereby providing an indication of the value of the preselected parameter.

2. The device according to claim 1, wherein the first resistor is a manually adjustable resistor.

3. The device according to claim 2, wherein the resistance value of the first resistor is adjusted upon replacing the sensor.

4. The device according to claim 1, further comprising a probe plug connector, the probe plug connector containing the first and second resistors in a single structural unit.

5. The device according to claim 1, wherein the sensor and the first and second resistors are contained in a single structural unit.

6. The device according to claim 1, wherein the preselected parameter is an oxygen concentration in exhaust gas from an internal combustion engine of a motor vehicle.

7. The device according to claim 1, further comprising a controlling device, the controlling device containing the current measuring device.

* * * * *